(12) United States Patent
Sun et al.

(10) Patent No.: US 10,828,876 B2
(45) Date of Patent: Nov. 10, 2020

(54) STIMULI RESPONSIVE MATERIALS, METHODS OF MAKING, AND METHODS OF USE THEREOF

(71) Applicant: University of Connecticut, Farmington, CT (US)

(72) Inventors: Luyi Sun, Storrs, CT (US); Songshan Zeng, Willington, CT (US)

(73) Assignee: UNIVERSITY OF CONNECTICUT, Farmington, CT (US)

(*) Notice: Subject to any disclaimer, the term of this patent is extended or adjusted under 35 U.S.C. 154(b) by 131 days.

(21) Appl. No.: 15/680,352

(22) Filed: Aug. 18, 2017

(65) Prior Publication Data

US 2018/0050524 A1   Feb. 22, 2018

Related U.S. Application Data

(60) Provisional application No. 62/376,987, filed on Aug. 19, 2016.

(51) Int. Cl.
| | |
|---|---|
| B32B 27/30 | (2006.01) |
| C08F 16/06 | (2006.01) |
| C08G 77/04 | (2006.01) |
| C07D 311/82 | (2006.01) |
| C09C 1/48 | (2006.01) |
| C08L 9/00 | (2006.01) |
| C08L 55/02 | (2006.01) |
| C08F 20/06 | (2006.01) |
| C08F 14/18 | (2006.01) |
| C01G 23/047 | (2006.01) |
| C08L 21/00 | (2006.01) |
| C07D 493/10 | (2006.01) |

(Continued)

(52) U.S. Cl.
CPC .............. *B32B 27/30* (2013.01); *C01F 17/32* (2020.01); *C01G 23/047* (2013.01); *C07D 311/82* (2013.01); *C07D 493/10* (2013.01); *C08F 14/18* (2013.01); *C08F 16/06* (2013.01); *C08F 20/06* (2013.01); *C08G 77/04* (2013.01); *C08L 9/00* (2013.01); *C08L 21/00* (2013.01); *C08L 55/02* (2013.01); *C09C 1/48* (2013.01); *C09D 129/04* (2013.01); *C09D 129/14* (2013.01); *C08K 2003/2241* (2013.01)

(58) Field of Classification Search
None
See application file for complete search history.

(56) References Cited

U.S. PATENT DOCUMENTS

| | | | |
|---|---|---|---|
| 8,815,771 B2 | 8/2014 | Chopra et al. | |
| 2015/0218337 A1* | 8/2015 | Studart | B82Y 30/00 428/215 |
| 2017/0335114 A1* | 11/2017 | Lee | G02B 1/14 |

FOREIGN PATENT DOCUMENTS

| | | | |
|---|---|---|---|
| JP | 2015052710 A | * | 3/2015 |
| WO | 2012080467 A1 | | 6/2012 |
| WO | 2013093766 A1 | | 7/2013 |

OTHER PUBLICATIONS

Howell article ACS Appl. Mater Interfaces 7 3641-3646 (2015).*

(Continued)

*Primary Examiner* — Kenneth J Stachel
(74) *Attorney, Agent, or Firm* — Cantor Colburn LLP

(57) ABSTRACT

A mechanochromic system comprising a first inorganic/polymer composite layer; and a first elastomer layer bonded to the composite layer to form a composite/elastomer assembly, methods of making, and methods of use thereof are provided.

19 Claims, 12 Drawing Sheets

(51) Int. Cl.
    *C09D 129/14*     (2006.01)
    *C09D 129/04*     (2006.01)
    *C01F 17/32*     (2020.01)
    *C08K 3/22*     (2006.01)

(56) References Cited

OTHER PUBLICATIONS

Araki article Soft Matter 3 1456-1473 (2007).*
San-Miguel article Polymer 50 5884-5891 (2009).*
English translation of JP 2015-052710 (2015).*
Yin Applied Materials & Interfaces, 6, 2850-2857 (2014).*
Yin Adv Mate. 24 5441-5446 (2012).*
Accession No. 2004-168098 (2004).*
Accession No. 2014-571504 (2014).*
Cao, C. et al., "Harnessing Localized Ridges for High-Aspect-Ratio Hierarchical Patterns with Dynamic Tunability and Multifunctionality", Advanced Materials, 2014, vol. 26, pp. 1763-1770.
Chan, E. et al., "Mechanochromic Photonic Gels" Advanced Materials, 2013, vol. 25, pp. 3934-3947.
Lee, S. et al. "Switchable Transparency and Wetting of Elastomeric Smart Windows", Advanced Materials, 2010, vol. 22, pp. 5013-5017.
Reis, P., "Folded in hierarchy", Nature Materials, Dec. 2011, vol. 10, pp. 907-909.
Lee, E. et al., "Tilted Pillars on Wrinkled Elastomers as a Reversinly Tunable Optical Windo", Advanced Materials, 2014, vol. 26, pp. 4127-4133.
Kim, P. et al., Hierarchical folding of elastic membranes under biaxial compressive stress, Nature Materials, Dec. 2011, vol. 10, pp. 952-957.
Kim, P. et al., "Rational Design of Mechano-Responsive Optical Materials by Fine Tuning the Evolution of Strain-Dependent Wrinkling Patterns", Advanced Optical Materials, vol. 1, pp. 381-388.
Mäthger, L. et al., "Mechanisms and behavioural functions of structural coloration in cephalopods", J. R. Soc. Interface (2009) 6, S149-S163, doi:10.1098/rsif.2008.0366.focus, 15 Pages.
Zeng, S. et al., "Bio-inspired sensitive and reversible mechanochromisms via strain-dependent crack and folds", Nature Communications, Jul. 8, 2016, DOI: 10.1038/ncomms11802, 9 Pages.
Wong, H. et al., "The rheology and processing of 'edge sheared' colloidal polymer opals", Journal of Rheology (1978-present) 58, 397 (2014); doi: 10.1122/1.4862920, 14 Pages.
Zeng, S. et al., PMSE: Division of Polymeric Materials Science and Engineering, 414—Stimuli Responsive Elastomer Based Hybrids with Tunable Multifunctionality, ACS National Meeting, Boston, 2015, Abstract Only.
Mackie G. & Mackie G., "Mesogloeal Ultrastructure and Reversible Opacity in a Transparent Siphonophore", Department of Zoology, vie et milieu, Serie A. Biologie marine, vol. 18, pp. 47-67, 1967, University of Alberta, Edmonton, Canada, 31 Pages.

* cited by examiner

US 10,828,876 B2

STIMULI RESPONSIVE MATERIALS, METHODS OF MAKING, AND METHODS OF USE THEREOF

CROSS-REFERENCE TO RELATED APPLICATIONS

This application claims priority to U.S. provisional application Ser. No. 62/376,987, filed Aug. 19, 2016, the contents of which is hereby incorporated by reference it its entirety.

BACKGROUND

Mechanochromic devices change transparency and/or color in response to mechanical stimuli, making them attractive for a wide range of applications in smart windows, strain sensors, encryption, tunable wetting systems, and others. However, these devices are not widely available and require complicated preparation procedures and specialized equipment to make.

There remains a need for materials that change their optical qualities upon application of mechanical force.

BRIEF SUMMARY

A mechanochromic system, comprising: a first inorganic/polymer composite layer; and a first elastomer layer bonded to the composite layer to form a composite/elastomer assembly is provided.

In an embodiment, the polymer is water soluble. In an embodiment, the polymer is organic soluble.

A method of making a mechanochromic system, comprising: applying a layer of inorganic/polymer composite on a substrate; applying a layer of elastomer on a top surface of the composite to form a composite/elastomer assembly; curing the composite/elastomer assembly; and removing the composite/elastomer assembly from the substrate is provided.

A method of using a mechanochromic system, comprising: providing a composite/elastomer assembly as described herein; applying a 50 to 70% uniaxial tensile pre-stretch to the composite/elastomer film; releasing the pre-stretch; applying an up to 50% uniaxial tensile strain to the composite/elastomer film, wherein the mechanochromic system undergoes a reversible transparency change, fluorescent luminescence change, fluorescent color change, encryption concealment change, or a combination comprising at least one of the foregoing is provided.

The above described and other features are exemplified by the following detailed description.

DETAILED DESCRIPTION

Figure 1:
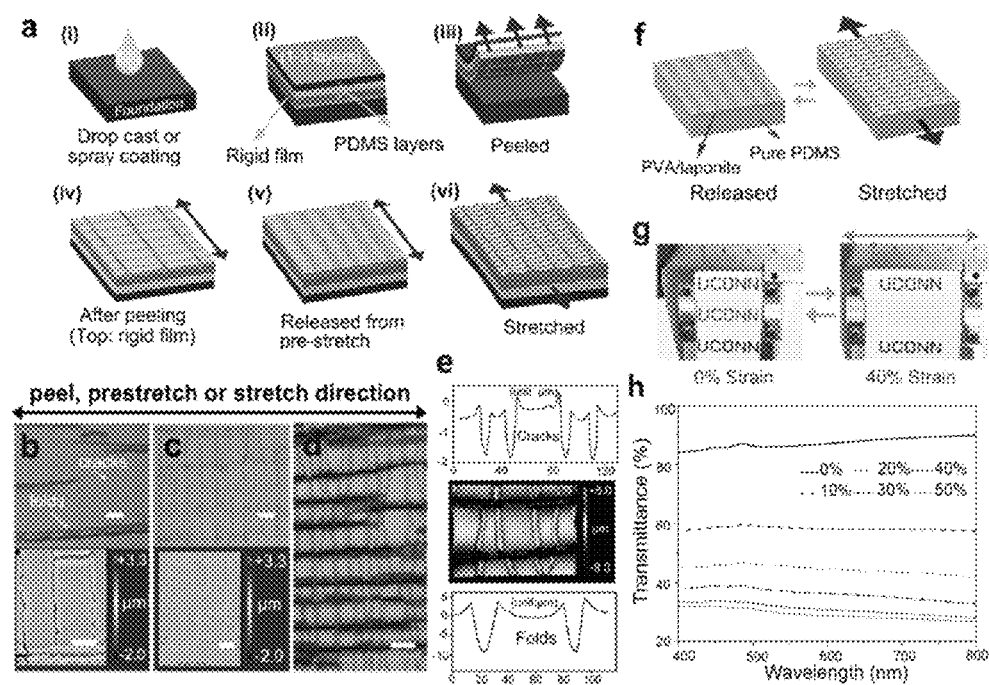
FIG. 1 shows preparation of mechanochromisms and strain responsive properties of transmittance change mechanochromism (TCM).

The materials, methods, and uses described herein are further illustrated by the following non-limiting description.

The inventors hereof have unexpectedly found a scalable, simple, and low cost method of preparing stimuli-responsive materials with tunable multi-functionality. In an embodiment, a bilayer structure of laponite/PVA composite thin film bonded to an elastomeric polydimethylsiloxane (PDMS) substrate is prepared to achieve tunable optical transmittance, wettability, as well as mechanochromism. The transition between a transparent and opaque state can be achieved by uniaxially stretching and releasing the layer. The system shows different surface morphologies and strain-responsive optical properties by changing the composition of the nanocomposite layer. Systems with tunable surface hydrophobicity, coefficient of friction, and conductivity are provided. In an embodiment, the system has a water-induced shape memory effect. The systems and methods can be used for many purposes, including smart window or dynamic optical switches with mechanically tunable transmittance. The mechanochromism can be used as a fluorescent strain sensor that can be used to monitor strain formation in a material, in an embodiment. The tunable wettability can be used for self-cleaning surfaces, or in microfluidic applications, in embodiments.

Described herein is a mechanochromic system, comprising: a first inorganic/polymer composite layer; and a first elastomer layer bonded to the composite layer to form a composite/elastomer assembly. In an embodiment, the polymer comprises polyvinylalcohol, polyvinyl butyral, polycarbonate, poly(methyl methacrylate), polyacrylates, polystyrene sulfonate, polyacrylic acid, polyethylenimine, other water or organic soluble polymers, or a combination comprising at least one of the foregoing. In an embodiment, the elastomer comprises polyurethane rubber, polyacrylate rubber, acrylic rubber, natural rubber, fluoroelastomers, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), polydimethylsiloxane (PDMS), or a combination comprising at least one of the foregoing. In an embodiment, the elastomer is a fluoroelastomer and the fluoroelastomer comprises a copolymer of hexafluoropropylene and vinylidene fluoride; a terpolymer of tetrafluoroethylene, vinylidene fluoride and hexafluoropropylene; perfluoromethylvinylether; or a combination comprising at least one of the foregoing.

The inorganic comprises metals, metal salts, nonmetals, nonmetal salts, metalloids, metalloid salts, or a combination comprising at least one of the foregoing. The inorganic can be 0-dimension particle, 1-dimension rods/tubes/fibers, 2-dimension sheets; or a combination comprising at least one of the foregoing. The inorganic can be titanium dioxide. In an embodiment, the inorganic comprises titanium dioxide; laponite; aluminum oxide; magnesium oxide; zinc(II) oxide; montmorillonite; halloysite; kaolinite; Au; Pd; Ag; Al; or a combination comprising at least one of the foregoing. The inorganic can be laponite.

As used herein, "bonded" or "connected" means either physically or chemically connected, or a combination comprising at least one of the foregoing. "Layer" does not necessarily mean there is a uniformly thick coating, or that there are no defects, holes, thickness deviations, or other imperfections.

Deformation controlled surface engineering via strain-dependent cracks and folds was used to produce four mechanodependent devices: (1) transparency change mechanochromism (TCM), (2) luminescent mechanochromism (LM), (3) color alteration mechanochromism (CAM), and (4) encryption mechanochromism (EM), based on a simple bilayer system which exhibit a wide scope of mechanochromic response with excellent sensitivity and reversibility. The TCM device can reversibly switch between a transparent and opaque state, in an embodiment. The LM can emit intensive fluorescence as stretched with an ultrahigh strain sensitivity, in an embodiment. The CAM can turn fluorescent color from green to yellow to orange as stretched within 20% strain, in an embodiment. The EM device can reversibly reveal and conceal any desirable patterns, in an embodiment.

Deformation controlled surface engineering to achieve various mechanochromisms through a series of well-designed optical devices is described here. One aspect is a hybrid bi-layer material system comprising a rigid thin film bonded onto a soft substrate to accomplish four different types of mechanochromisms: (1) transparency change mechanochromism (TCM), (2) luminescent mechanochromism (LM), (3) color alteration mechanochromism (CAM), and (4) encryption mechanochromism (EM).

All these devices can rapidly and reversibly change their optical appearance when subjected to small mechanical stimuli (<40% uniaxial tensile strain, for example; all the mechanical strain discussed herein are uniaxial tensile strain). For example, the TCM device can reversibly switch between transparent and opaque state. The LM can emit intensive fluorescence as stretched with an ultrahigh strain sensitivity as compared to the electrical resistance based strain sensor. The CAM can turn fluorescent color from green to yellow to orange as stretched within 20% strain. The EM device can reversibly reveal and conceal any desirable patterns within 17% strain. The surface structures and morphologies of these devices are controlled during the deformation, that is, the evolution of the cracks and invaginated folds in the top thin film.

Design and general preparation procedures for all the mechanochromisms is described next. To obtain a highly sensitive and reversible TCM, in an embodiment, the device comprises a transparent rigid film (made of polyvinyl alcohol (PVA)/laponite composite) tightly bonded to a soft polydimethylsiloxane (PDMS), as shown in FIG. 1(f). The device can reversibly exhibit conspicuous visual change between a transparent state and an opaque state upon stretching and releasing within 40% strain (FIG. 1(g)). Although Applicant is not bound by any theory presented here, the high opaqueness in the stretched state is thought to be due to the excellent light trapping and scattering effect resulting from the strain dependent cracks and folds (FIG. 1(d) and FIG. 2(a)). It should be noted that this device can be fabricated using a facile and scalable method without the need to use any special equipment such as plasma, ultraviolet-ozone (UVO) radiation, or lithography. For the LM, a rigid ultraviolet (UV) shielding film is firmly adhered to a soft PDMS substrate that comprises a fluorophore layer and a reflector layer (see FIG. 3(b)). When the device undergoes stretching, highly distributed cracks develop in the UV shielding layer, and the crack size is correlated to the applied tensile strain. These cracks act as "gates" to adjust the exposure area of the fluorophore and the concomitant UV excited fluorescent intensity. The additional reflector layer at the bottom can enhance the fluorophore luminescence via reflection, leading to a significant improvement of the strain-responsive luminescent performance. Only 5% strain is sufficient to change the visibility of the device from a nonluminous state to an apparently eye-detectable luminescent state. In an embodiment, the fluorophore comprises a rhodamine; a fluorescein; a coumarin; a cyanine; a quinine;

a anthraquinine; an acridine; an oxazine; a fluorone; a phenanthridine; or a combination comprising at least one of the foregoing.

The structure of the CAM was similar to the LM, but in the CAM structure, a thin film of laponite/fluorescein with green fluorescence was coated atop the rigid UV shielding film, and the rigid layer was subsequently adhered to a soft layer that contained europium doped yttrium oxide ($Y_2O$:$Eu^{3+}$, emitting orange fluorescence) (see FIG. 4(a)). The device exhibits green fluorescence in the released state with all the cracks closed. Upon only 20% strain, the crack opening in the rigid film can significantly increase the exposure area of PDMS/$Y_2O_3$:$Eu^{3+}$ layer, generating orange fluorescence. Thus, the device turns the fluorescent color from green to yellow to orange along an increasing strain (see FIG. 4(b)). The system described here allows fluorescence without specialized synthetic dyes incorporated into a polymer matrix.

For the EM, the device was modified based on the LM where the encrypted information was embedded in the soft PDMS layer, as shown in FIG. 5(b). As a result, the information "input" to the device can be reversibly revealed and concealed upon stretching and releasing the sample (0%-17% strains) under UV light (see FIG. 5(b)).

The preparation of the aforementioned mechanochromisms was generally similar, as illustrated in FIG. 1(a). FIG. 1 shows preparation schemes of mechanochromisms and the strain-dependent surface morphologies and optical properties of TCM. FIG. 1(a) shows the general preparation approach for all the mechanochromisms (the arrows indicate the peel, pre-stretch, or stretch direction). FIG. 1(b)-(e) shows optical microscope images and surface profiles of the topmost rigid layer of the TCM; (b) immediately after being peeled from the foundation (corresponding to step (iv)); (c) release from a 60% strain pre-stretch (corresponding to step (v)), (d)-(e) stretched at 40% strain (corresponding to step (vi)). FIG. 1(f) shows a design scheme for the TCM. FIG. 1(g) shows digital photos demonstrating the TCM. FIG. 1(h) shows strain-dependent transmittance of the TCM. All the scale bars represent 20 μm. All the objects in the schematic diagram are not drawn to scale.

Figure 17:
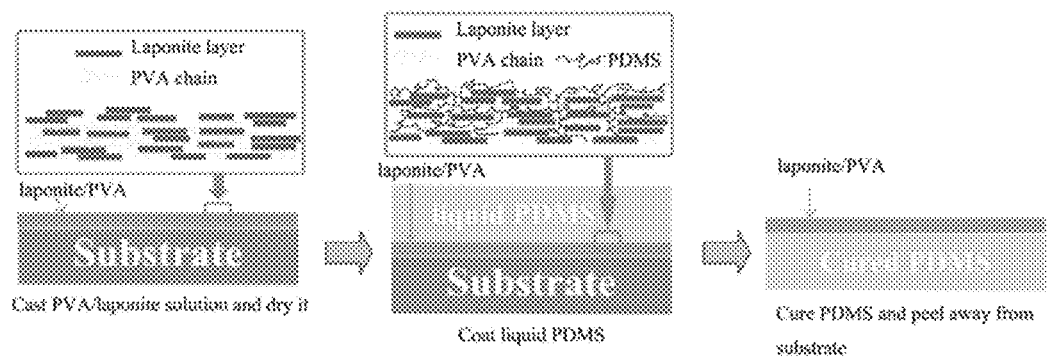
FIG. 17 shows an exemplary preparation of laponite/PVA and PDMS bilayer structure.

Initially, a thin rigid composite film (could contain multilayers) was prepared by drop-casting or spray coating on a plastic foundation followed by the treatment of vinyl-functionalized silane vapor (step (i)). A liquid PDMS substrate was then cast atop the thin film and then thermally cured to form a thick soft layer (about 1 mm). This process can be repeated to cast multiple PDMS layers containing different functional components (step (ii)). The approach allows the low surface energy liquid PDMS (20.4 mN/m) to form an intimate contact and strong adhesion with the rigid thin film via covalent bonding. The device was then carefully peeled away from the foundation along one direction (step (iii)). These steps are also shown in FIG. 17, in an embodiment. After peeling, the topography of the rigid film exhibited periodical longitudinal cracks vertical to the peeling direction and transverse folds perpendicular to the cracks due to the compressive force as a result of the Poisson effect (step (iv)). However, this rough surface would deteriorate the transparency at the released state for the TCM, and the low crack density would also limit the strain-dependent performance for all the mechanochromisms. Thus, a pre-stretch of 60% strain was applied to increase the densities of the cracks and the folds in the rigid film. It should be noted that such a pre-stretch results in damage at the edges and valleys of the folds. Upon release, the rigid film restored to a flattening surface with dense cracks fully closed (step (v)).

The typical optical microscope images and surface profiles at the aforementioned procedures are shown from FIG. 1(b) to 1(e). When the device was stretched again, the rigid thin film showed a quasi-orthogonal periodic network with distributed longitudinal cracks and transverse invaginated folds (step (vi) and FIGS. 1(d) and 1(e)) due to the mismatch of stiffness between the rigid thin film and the soft PDMS substrate and the strong interface bonding in between. All these devices exhibited exceptional reversible and durable performance, which can be repeated for virtually infinite cycles between step (v) and step (vi) within the elasticity range of PDMS (see FIG. 6-9).

Strain-dependent optical properties and localized folds in the TCM are described next. The correlation between the optical transmittance and the applied strain for the TCM is demonstrated in FIG. 1(h). The sample exhibited high transparency (transmittance>88% at 600 nm) in the released state (FIG. 1(g)). With applied strains, the transmittance dropped sharply by nearly half in the first 20% strain due to the light scattering and trapping effect resulting from the invaginated folds and longitudinal cracks at the microscale. Impressively, the sample became highly opaque (transmittance<29% at 600 nm) (FIG. 1(h)) when being stretched to 40% strain. Such performance can be repeated for almost infinite cycles (>50,000 times) without observable changes in the optical properties (FIG. 6), making them useful for applications in smart windows and dynamic optical switches. As shown in the surface profile image (FIG. 1(e)), the opening size of the longitudinal cracks was increased up to about 7.9 micrometers (μm) with an average depth of about 1.7 μm as stretched to 40% strain. Meanwhile, the crest-to-bottom depth of the invaginated folds increased sharply to 13.3 μm with a crest-to-crest distance of 17.8 μm. These folds show a unique feature of sharp double ridges (or edges), indicating that the ridges undergo out-of-surface traction, while the valley experiences into-surface traction. These folds show a high respect ratio (Ω) of 0.75 (defined as the ratio between the crest-to-bottom depth (D) to crest-to-crest distance (A)) when subjected to 40% strain, which accounts for the significantly enhanced light trapping capability and the surface hydrophobicity. As a result, the device can change between transparent and opaque states in response to small strains (0-40% strain). This unique fold-ridge formation mechanism was simulated through a three dimensional (3D) finite element (FE) model using the commercially available software ABAQUS (version 6.14), as shown in FIG. 2(a).

Figure 2:
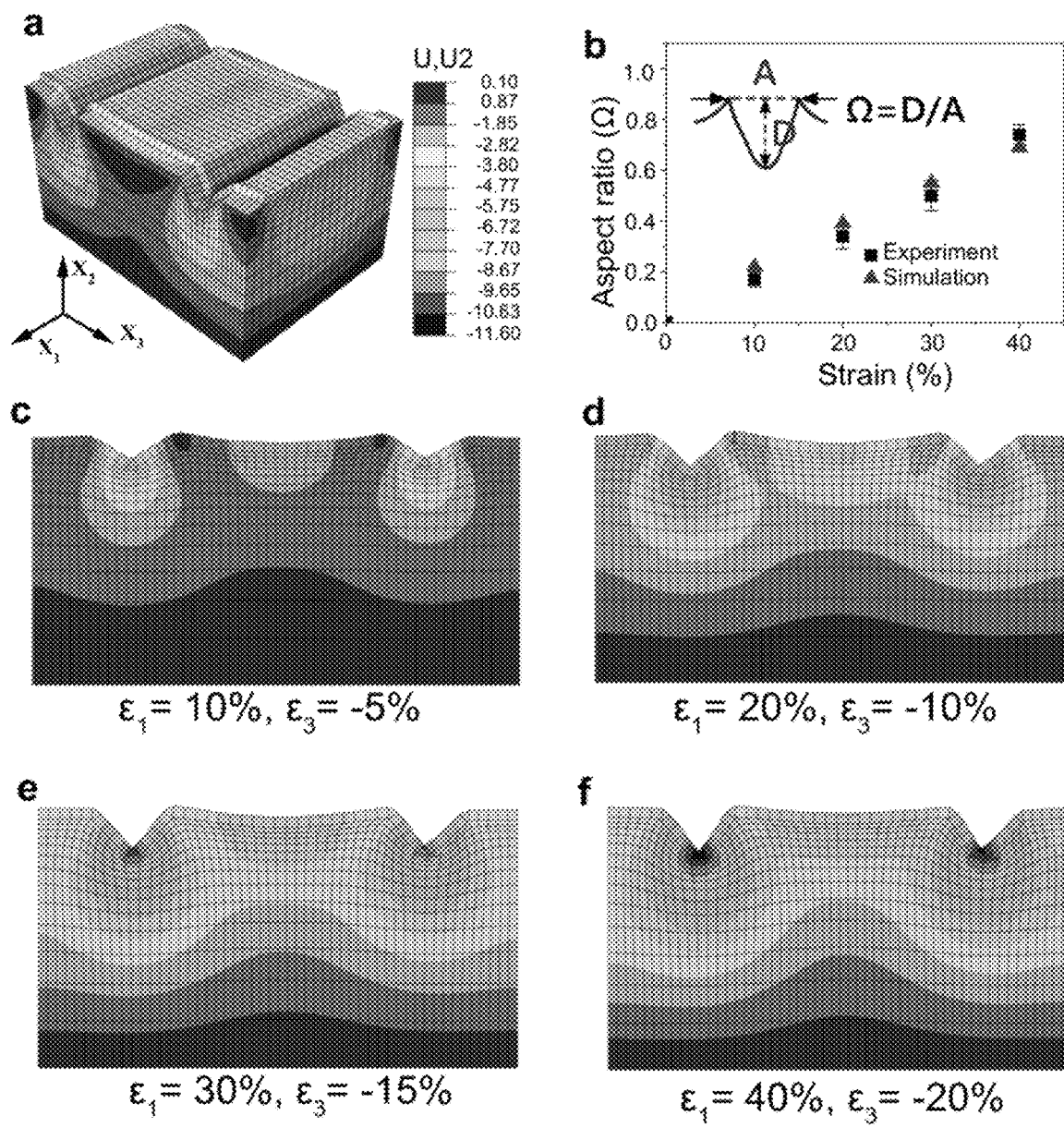
FIG. 2 shows simulated or experimental results of folds in the TCM.

FIG. 2 shows simulated or experimental results of folds in the TCM. FIG. 2(a) shows 3D finite element simulation of folding as subjected to 40% tensile strain in $X_1$ direction with accompany of 20% compression in $X_3$ direction due to the Poisson effect. FIG. 2(b) shows experimental and simulated result of the folding's aspect ratio with different applied tensile strains; error bars are defined as s.d.; (c)-(f) simulated evolution of folding (visualized as 2D cross-section on $X_1$ direction) with an increasing tensile strain on the $X_1$ direction. All figures using the same stress scale bar as applied in FIG. 2(a).

Figure 10:
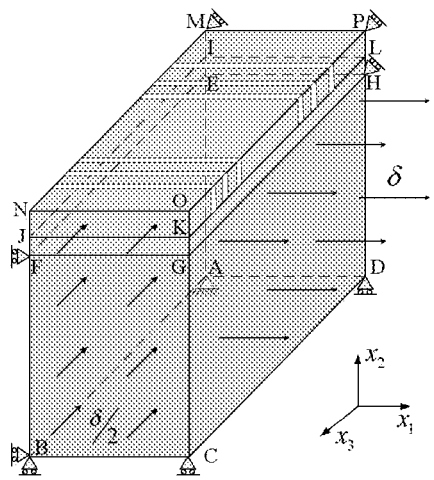
FIG. 10 shows a finite element model for the fold-ridge mechanism.
Figure 11:
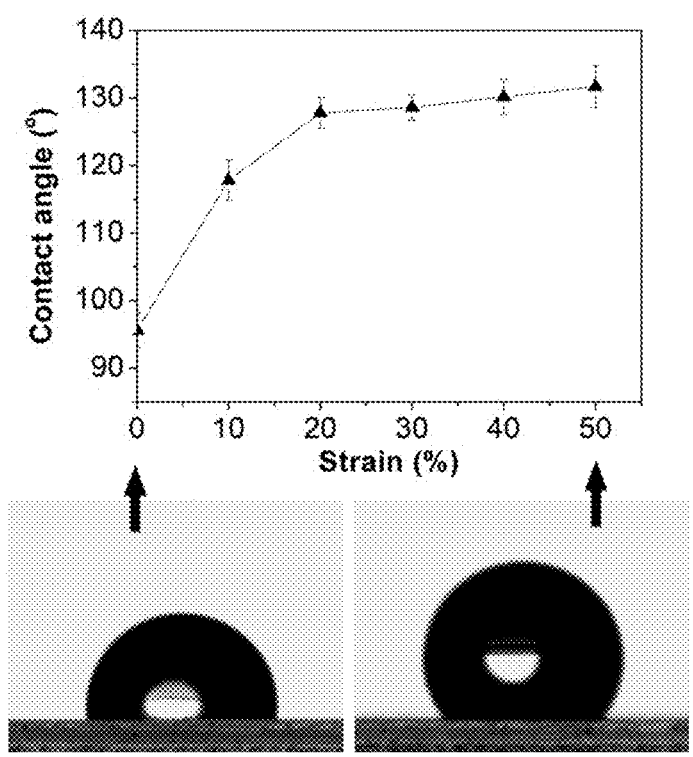
FIG. 11 shows correlation of contact angle with applied strain on the topmost surface of transparency change mechanochromism. The sample was immersed in a 1 weight percent glutaraldehyde solution for 1 hour to form a PVA/laponite crosslinked network prior to test in order to achieve good water resistance.

The rigid thin film was tied onto the PDMS substrate by enforcing the displacement continuity at the interface. The modeling details, including the geometry, boundary conditions, and material properties, are given herein and in FIG. 10. Reversible fold-ridge formation is provided by introducing damage in the thin film, which results from the development of invaginated folds during the pre-stretch stage. These softening areas, modeled as a damage solid by reducing the Young's modulus to 1% of the modulus of the pristine thin film, promote the formation of high-aspect-ratio folds in the stretched state, resulting in an opaque state due to the light trapping capability of these folds. FIG. 2 (c)-(f) show the evolution of the folding geometry (cross section cut along the tensile direction) with increasing strains obtained from the FE simulation. The aspect ratio computed using the FE model is in good agreement with the experiment, as shown in FIG. 2 (b). The surface wettability of the TCM can be tuned upon elongation strain (from 0-50%, see FIG. 11), which is valuable for many applications, including those in liquid transportation, smart microfluidics devices and integrated surfaces and devices. FIG. 11 shows the measured contact angle of the thin film as a function of the applied uniaxial strain. The contact angle increased from 95° at 0% strain to 130° at 40% strain. This is because of the formation of a rougher surface at higher strain as discussed elsewhere herein. It was observed that the aspect ratio of the folds (defined as the ratio of the amplitude to the distance between neighboring crests) is about 0.20 at 10% strain and about 0.95 at 40% strain. At a low strain with a low fold aspect ratio (<10%), water droplets are expected to easily penetrate into the valleys in folds, creating a continuous stable three-phase (solid-liquid-gas) contact line with high water adhesion and a low contact angle. At a higher strain (>40%) with a high aspect ratio, a large volume of air trapped beneath the liquid, which prevents the penetration of water droplets into the valley, resulting in poor water adhesion. In FIG. 11, the sample was immersed in a 1 wt % glutaraldehyde solution for 1 h to form a PVA/laponite crosslinked network prior to test in order to achieve good water resistance.

Figure 3:
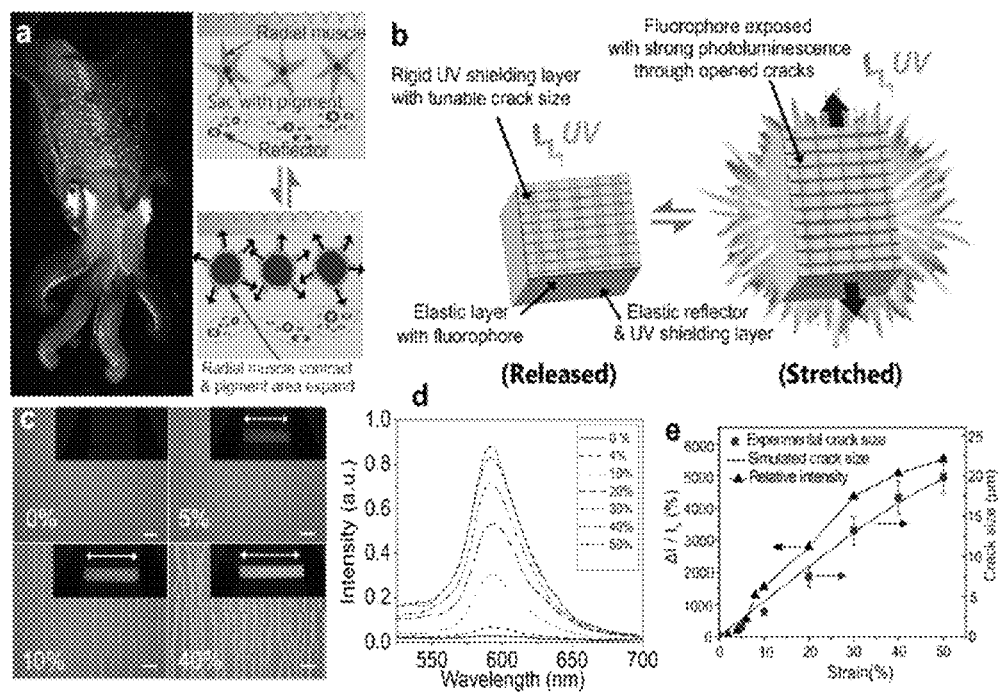
FIG. 3 shows design strategy and mechanical switchable fluorescence of the luminescent mechanochromism (LM).

Mechanical responsive fluorescence and crack size evolution of the LM are described next. FIG. 3 shows design and mechanical switchable fluorescence of the LM. FIG. 3(a) (Left) cephalopods (squid) showing chromatophore on skin (photo courtesy of Nhobgood (Own work) (CC BY-SA 3.0)) and (right) the coloration mechanism adopted by cephalopods. FIG. 3(b) shows the reversible LM. FIG. 3(c) shows optical microscope images showing the distribution and size of the longitudinal cracks upon strain in the LM (all the scale bars represent 100 μm); the insets are digital photos of this device experiencing corresponding strains under UV light (λ=365 nm) (white arrow indicating stretch direction). FIG. 3(d) shows fluorescent spectra of the LM as a function of strain (Excitation wavelength of UV=365 nm). FIG. 3(e) shows relative fluorescence intensity ratio at each strain to released state ($\Delta I/I_0$=intensity of certain strain/intensity of 0% strain-1) and the experimental and simulated cracks size evolution with strain for LM. Error bars are defined as s.d.

Since $TiO_2$ has a high refractive index (2.61 at 600 nm) and an excellent UV blocking capability through absorption, scattering, and reflection, the $TiO_2$/PVA (mass ratio=4:1) composite was utilized as the UV shielding layer in the LM (see FIG. 3(b)). The soft PDMS substrate includes a rhodamine filled luminescent layer and a $TiO_2$ filled reflector reflective layer, as shown in FIG. 3(b). The structural reflector can not only shield the UV light from other angles, but also significantly improve the overall fluorescence intensity by reflecting the luminescence from fluorophore. FIG. 3(c) shows that the device has no eye-detectable fluorescence at the released state with cracks closed in the rigid thin film. When stretched to 5% strain, the device displays conspicuous luminescence with the presence of the open cracks that are shown as bright strips in the background under an optical microscopy (see FIG. 3(c)), indicating the remarkable strain responsive sensitivity of this device. The fluorescence spectra (see FIG. 3(d)) and relative intensity ratio (RIR) (=(intensity of certain strain/intensity of 0% strain-1) (see FIG. 3(e)) as a function of strain quantitatively demonstrate the variation of strain-dependent luminescence. Impressively, when being stretched to 40% strain, the device displays a strong luminescence increased by 55 times in RIR (see FIG. 3(e)) with a crack opening size of 18 μm. For electrical resistance strain sensors, their gauge factor is defined as (dR/R)/(dL/L), where R is the resistance and L is the length. The gauge factor for a conventional metal sensor is about 2.0 and the value for a polymer composite (such as PDMS/carbon black) is about 20. Similarly, the slope is defined (=(dI/I)/(dL/L)) of the RIR curve in FIG. 3(e) as the gauge factor for the samples. The gauge factor of the device is 123.7 (0-50% strain), which is significantly higher than many reported gauge factors in the electrical resistance strain sensors. This ultrahigh sensitivity of the strain-responsive luminescence in the LM can be attributed to the strain-induced opening of the originally closed cracks, a high crack density with small inter-cracks spacing (spacing size=about 41 μm), and the strong reflection from the structural reflector. The evolution of RIR can be correlated to the exposure area of fluorophore which is dictated by the crack opening size. Thus, both the crack opening size and RIR are evolved in a similar trend. Here, these opening cracks act as micro-scale "gates" that allow the exposure of fluorophore to the UV light and "switch on" the corresponding fluorescence. To demonstrate the importance of the $TiO_2$ filled reflective layer, a LM device with a PDMS/carbon black reflector was prepared. It was found that the RIR of this device was about 1.2 at 40% strain, which is about 46 times smaller than the one using the PDMS/$TiO_2$ reflector. Thus, the strong reflective luminescence of the fluorophore from the reflector is another key factor to enhance the strain responsive fluorescence.

Figure 12:
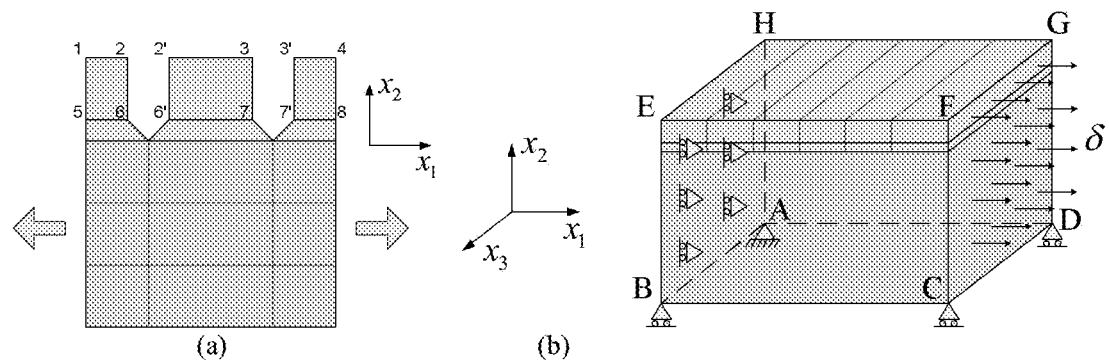
FIG. 12 shows a finite element model for crack opening response. (a) Dummy nodes were used to represent crack opening. (b) Boundary conditions.
Figure 13:
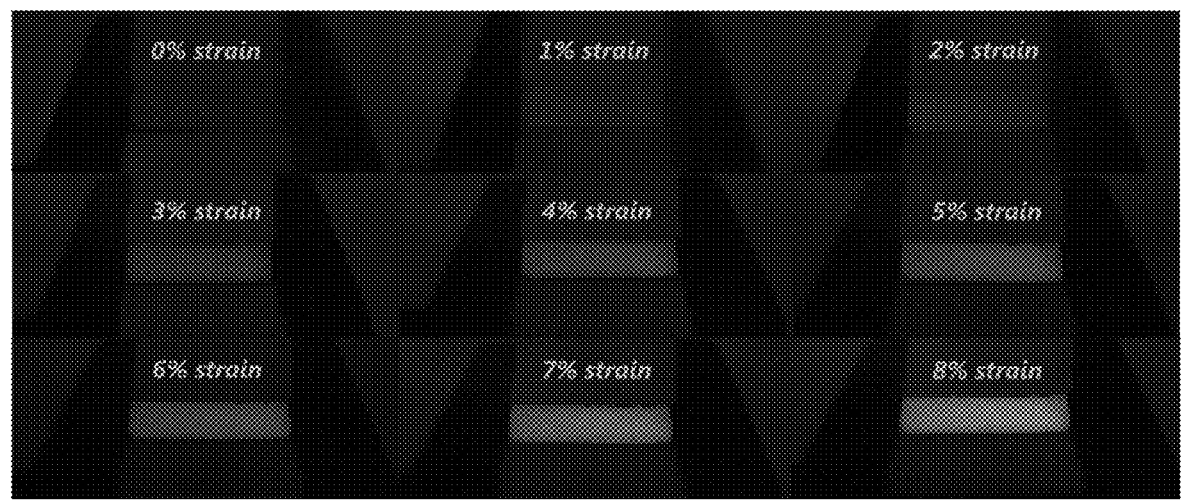
FIG. 13 shows digital photos showing fluorescent intensity change as a function of applied tensile stain (0-8%) in the luminescent mechanochromism (UV light source: wavelength=365 nm).
Figure 14:
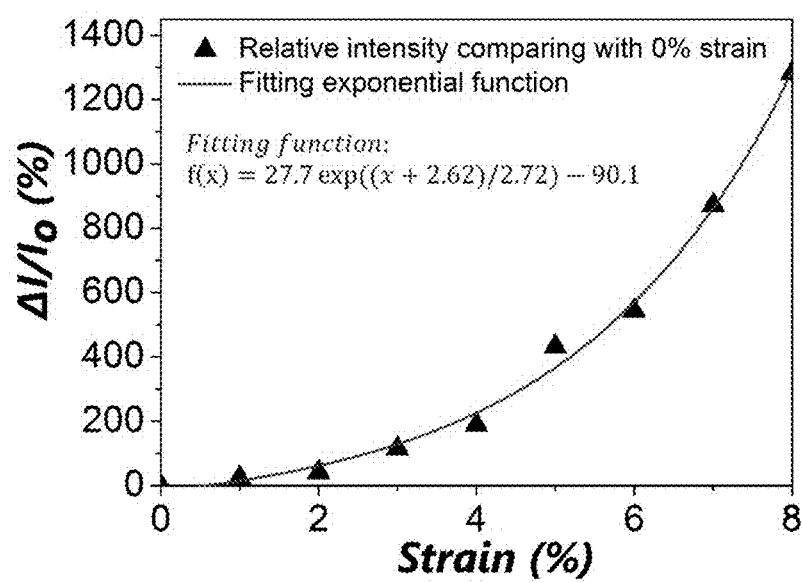
FIG. 14 shows the change of relative intensity ratio as a function of applied strain (0-8%) and the corresponding exponential function fitting in the luminescent mechanochromism.

The evolution of the crack size in the LM was simulated using a 3D FE model similar to that for the fold-ridge formation in the TCM, in which the displacement continuity was enforced across the interface between the rigid thin film and the PDMS substrate. The distributed cracks in the thin film, which were developed after the pre-stretch stage, were modeled as dummy nodes embedded at the crack interface. These cracks were fully opened across the thin film and arrested in the PDMS substrate, as schematically shown in FIG. 12. The simulation captures the nonlinear crack opening response for strains greater than 30%, which are in good agreement with the experimental results, as shown in FIG. 3(e). In the small-strain regime (ε<20%), the computed crack size grows linearly with increased strains, while the experiment shows a non-linear increase of crack size and RIR. The computed crack size is slightly larger than the experimental result due to the fact that the model neglects the cohesive force at the crack interface. The strong intermolecular hydrogen bonding in the thin film (PVA/$TiO_2$ layer) allows the crack to be fully closed at the released state. When the film-substrate system is subjected to small strains, there exist cohesive forces that reduce the crack opening size, resulting in an exponential growth of the RIR in the range of 0-8% strain (FIG. 13 and FIG. 14). However, the effect of cohesion disappears once the crack is widely open with the fracture energy completely dissipated.

Figure 4:
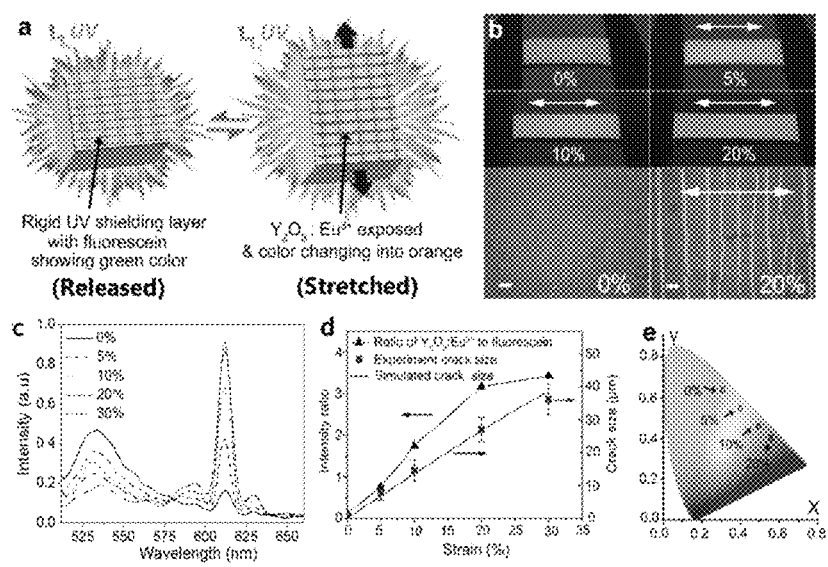
FIG. 4 shows design strategy and mechanical responsive color change of the color alteration mechanochromism (CAM).

Strain-induced color variation of the CAM and the performance of the EM are described next. FIG. 4 shows the design strategy and mechanical responsive color change of the CAM. FIG. 4(a) shows a design scheme of the reversible CAM. FIG. 4(b) shows digital photos of CAM at different strains (0%-20%) under UV light (λ=254 nm) and the corresponding optical microscope images of crack size and distribution at 0% and 20% tensile strain (white arrow indicating stretch direction). FIG. 4(c) shows fluorescent spectra of the CAM as a function of strain; (Excitation wavelength of UV=247 nm). FIG. 4(d) shows the change of intensity ratio of $Y_2O_3$:$Eu^{3+}$ to fluorescein with strain in the CAM and the corresponding experimental and simulated crack size evolution with strain; error bars are defined as s.d. FIG. 4(e) shows the color change of CAM at different strains illustrated in the CIE color space.

Figure 15:
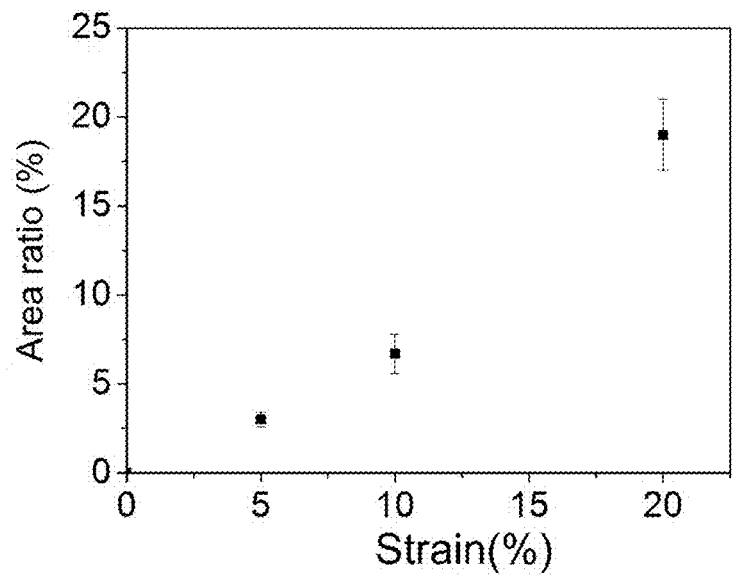
FIG. 15 shows the area ratio of opening crack to non-opening-crack surface in CAM.

The CAM is achieved by coating a laponite/fluorescein film with green fluorescence atop the $TiO_2$/PVA thin film, which is bonded to a PDMS layer containing $Y_2O_3$: $Eu^{3+}$ with orange fluorescence (see FIG. 4(a)). The overall fluorescent color is determined by the linear combination of green and orange fluorescence. To achieve a conspicuous color alternation in small strains less than 20%, it is necessary to consider the ratio of the exposure areas of the two fluorophores which equals to the area ratio of opening cracks (corresponding to $Y_2O_3$:$Eu^{3+}$) and non-opening-cracks surface (corresponding to fluorescein). For example, at 20% strain, this ratio can be calculated from the area of bright strips (corresponding to opening cracks) divided by the area of dark background (corresponding to non-opening-cracks surface) in an optical microscope image shown in FIG. 4(b). This ratio (FIG. 15) is about 19% at 20% strain, suggesting that the fluorescent intensity and the concentration of $Y_2O_3$: $Eu^{3+}$ need to be much higher than those of fluorescein to compensate the small exposure area. Thus, the concentrations of fluorescein and $Y_2O_3$:$Eu^{3+}$ were optimized to be $1 \times 10^{-8}$ mol/g and $4.3 \times 10^{-5}$ mol/g in their matrix, respectively, to maximize the strain-dependent color alternation performance. The fluorescent spectra (excited at 247 nm) as a function of strain (FIG. 4(c)) show two main peaks at 533 nm (from Fluorescein) and 612 nm (from the $^5D_0 \rightarrow ^7F_2$ transition of $Eu^{3+}$ in $Y_2O_3$:$Eu^{3+}$). The peak intensity at 533 nm gradually decreased with an increasing strain, while the peak intensity at 612 nm increased significantly. Notably, when the strain was increased to 5% or higher, new small peaks at 594 nm ($^5D_0 \rightarrow ^7F_1$ transition of $Eu^{3+}$) and 629 nm ($^5D_0 \rightarrow ^7F_2$ transition of $Eu^{3+}$) appeared owing to the fluorescence from $Y_2O_3$:$Eu^{3+}$. Extrapolated from the spectra, the intensity ratio of $Y_2O_3$:$Eu^{3+}$ to fluorescein generally increases in a non-linear fashion with an increasing strain (especially in the range of 20-30% strain), similar to the trend of crack opening size, as shown both in the experiment and simulation (see FIG. 4(d)). The intensity ratio of $Y_2O_3$: $Eu^{3+}$ to fluorescein is greater than 1 at 10% strain, and the ratio further increases to about 3.5 at 20% strain (see FIG. 4(d)). Here, the applied strains resemble a palette which can tune the fluorescent color of the device from green to yellow to orange within 20% strain (FIG. 4(b)). The FE model for computing the crack opening size is similar to that for the LM, but different values of crack spacing and depth were used in the simulation, as summarized in Table 1.

TABLE 1

Thin film thickness and crack spacing used in the FE model.

| | Film thickness (μm) | Crack spacing (μm) | Crack depth Average (μm) | Crack depth Standard deviation (μm) |
|---|---|---|---|---|
| LM | 5.1 | 41 | 7.0 | 1.2 |
| CAM | 13.9 | 125 | 18.3 | 4.5 |

The computed crack size is in good agreement with the experiment, as shown in FIG. 4(d). The model is able to capture the nonlinear increase in the crack opening figure size between 20-30% strains, which agrees with the experimental results of the intensity ratio and the crack size in the same strain range. The color coordinate in different strains are defined by the Commission Internationale de L'Eclairage (CIE) color space coordinate calculated from the strain-dependent fluorescent spectra. As shown in FIG. 4(e), the coordinates change linearly from green to yellow to orange with an increasing strain. Since the CIE coordinate is a linear combination of individual color coordinates, each coordinate represents a color combination of two individual fluorescence, one from fluorescein, and the other from $Y_2O_3$:$Eu^{3+}$. Only 20% strain is necessary to lead the device to reach orange (coordinate=0.55, 0.41) from green (0.30, 0.63) in original released state with a highly palpable color alternation and large color space crossing. Also, in this device, the transition between any two visible colors in the CIE coordinate other than green to orange can be achieved by simply incorporating the other corresponding fluorophores. Thus, a facile and universal method to prepare a highly sensitive and reversible mechanochromic device which can offer strain sensitive color-alternation signal to potentially visualize the occurrence of mechanical failure is provided.

Figure 5:
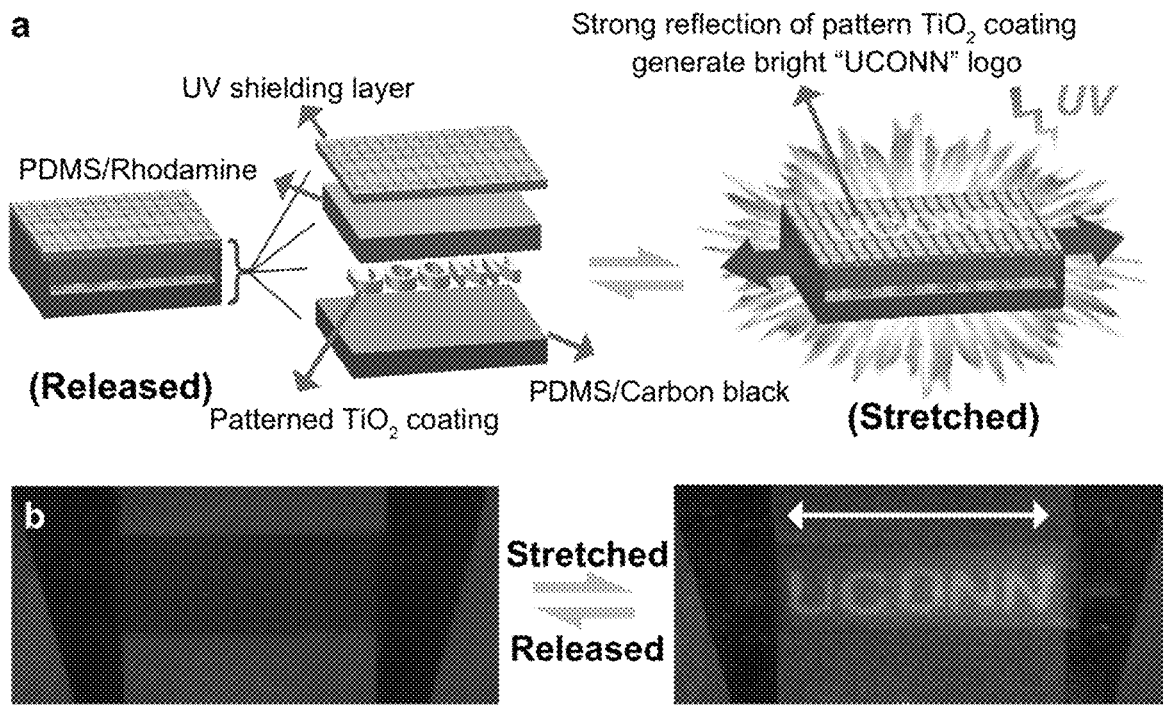
FIG. 5 shows design strategy and mechanical responsive encryption properties of the encryption mechanochromism (EM).
Figure 6:
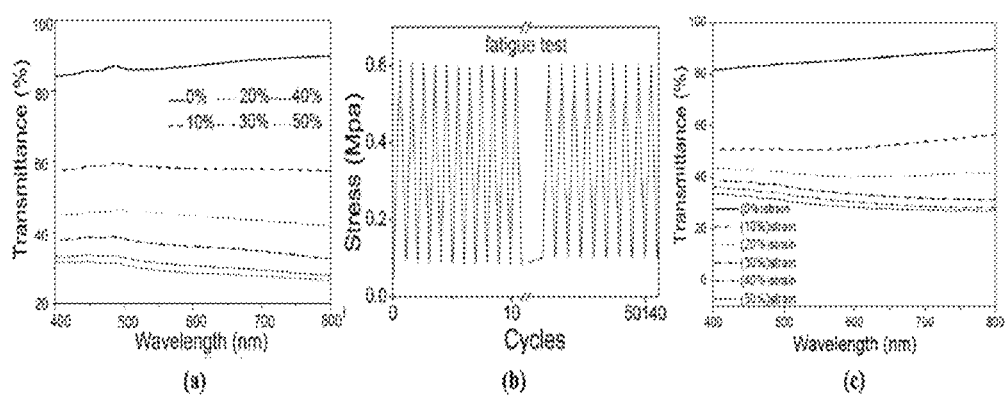
FIG. 6 shows (a) transmittance spectra of the TCM at different strains as tested before the fatigue test; (b) correlation between cyclic stress and cycles curve for the fatigue test; (c) transmittance spectra of the TCM at different strains as tested after the fatigue test.
Figure 7:
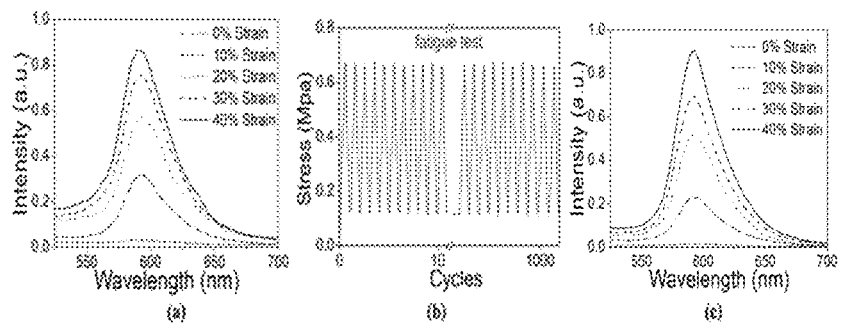
FIG. 7 shows fluorescence spectra of the LM at different strains as tested before the fatigue test (excitation wavelength of UV=365 nanometers (nm)); (b) correlation between cyclic stress and cycles curve for the fatigue test; (c) fluorescent spectra of the LM at different strains as tested after the fatigue test (excitation wavelength of UV=365 nm)
Figure 8:
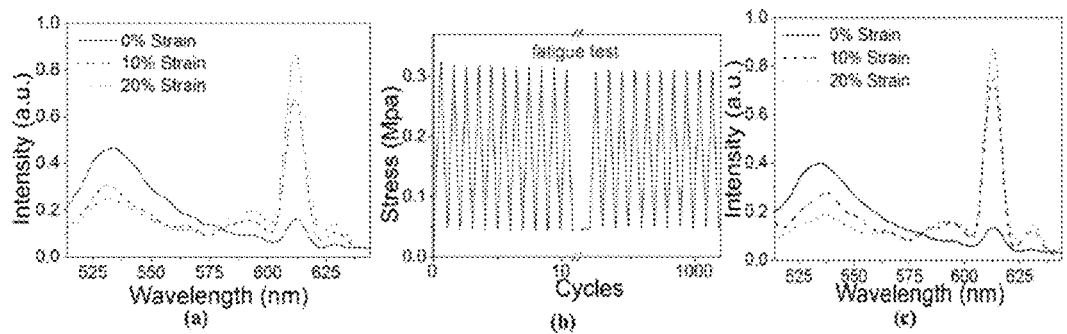
FIG. 8 shows (a) Fluorescence spectra of the CAM at different strains as tested before the fatigue test (excitation wavelength of UV=247 nm); (b) correlation between cyclic stress and cycles curve for the fatigue test; (c) fluorescence spectra of the CAM at different strains as tested after the fatigue test (excitation wavelength of UV=247 nm).
Figure 9:
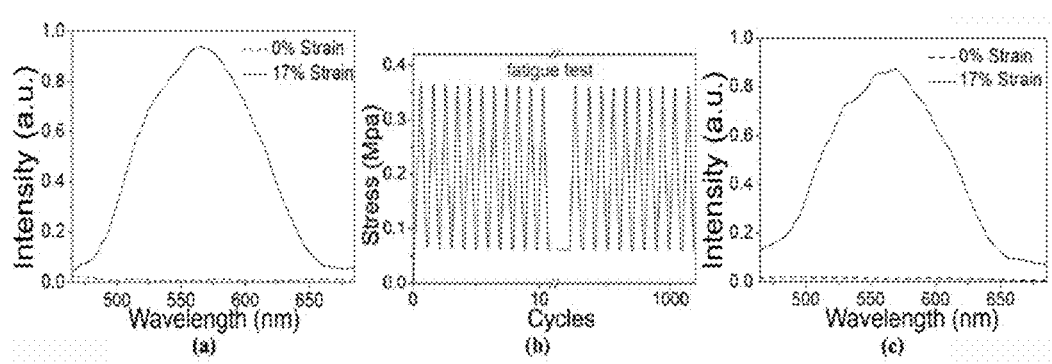
FIG. 9 shows (a) Fluorescent spectra of the EM at different strains as tested before the fatigue test (excitation wavelength of UV=365 nm); (b) correlation between cyclic stress and cycles curve for the fatigue test; (c) fluorescence spectra of the EM at different strains as tested after the fatigue test (excitation wavelength of UV=365 nm).
Figure 16:
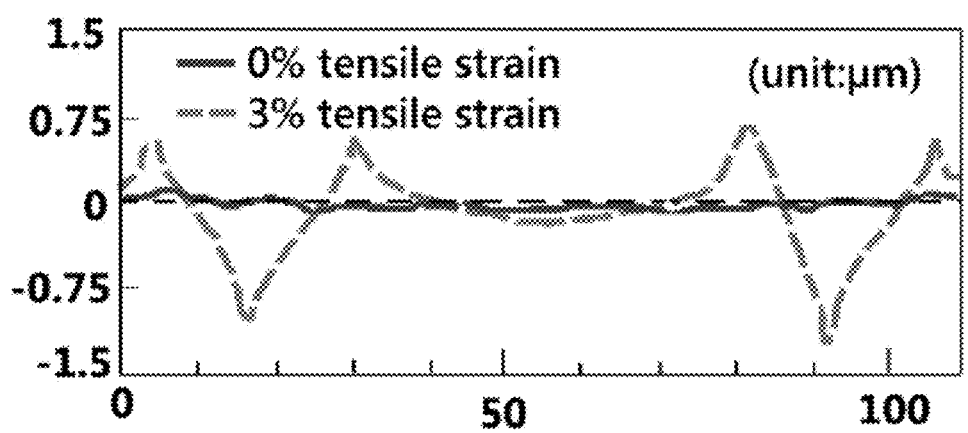
FIG. 16 shows the strain induced surface profile evolution of TCM on cross-section over $X_1$ direction as defined in FIG. 2. For the 0% tensile strain profile, the TCM experienced 0% tensile strain on $X_1$ direction and 0% compression strain on $X_3$ direction; for the 3% tensile strain profile, the TCM experienced 3% tensile strain on $X_1$ direction and 1.5% compression strain on $X_3$ direction.

Furthermore, the design of EM, which can be applied in encryption or display optics are shown in FIG. 5. FIG. 5(a) shows the design scheme of the reversible EM; (b) the hidden "UCONN" logo concealed at released state and revealed upon stretched to 17% strain with excellent reversibility. (Excitation wavelength of UV=365 nm). In FIG. 5(a), below the UV shielding layer and PDMS/Rhodamine, a patterned $TiO_2$ coating with "UCONN" logo is placed atop the PDMS/carbon black layer. As discussed above, the strain responsive sensitivity of the LM using PDMS/$TiO_2$ as a reflector is much higher than that using PDMS/carbon black. Stretching this device under UV light (λ=365 nm) at 17% strain allowed the area having the $TiO_2$ coating as the reflector to display the "UCONN" logo with much stronger luminescence than the other areas, while the letters can be well concealed as released (FIG. 5(b)). Thus, the hidden "UCONN" logo can be reversibly revealed and concealed upon stretching and releasing the sample (0%-17% strains) under UV light. In the device preparation procedures, liquid PDMS was added on the thin film via drop casting. This procedure allows part of the uncured PDMS to tightly bond with the thin film leading to a strong interface between the two layers. The strong interface is useful to achieve a highly reversible and durable strain-dependent optical performance. An alternative approach was used by directly casting the thin film onto the cured PDMS substrate and interfacial delamination was observed immediately after first stretching and releasing cycle. As a result, no conspicuous mechanical responsive transparency change was shown due to the poor interfacial adhesion. In addition, the preparation procedure can create localized closed cracks on the rigid thin film in the peeling and pre-stretch stage. These localized damages play an important role in directing the formation of folds in the step (vi) shown in FIG. 1(a). This folding structure is generated instantaneously as an ultra-small strain applied as shown in FIG. 16 (3% tensile strain applied with a corresponding 1.5% compression in the vertical direction due to the Poisson's effect). This unique feature can inspire the design of folding surface on other system. Also, the excellent light trapping capability of the high aspect ratio folding surface in the TCM can be used to increase the efficiencies of solar energy harvesting systems. In FIG. 16, for the solid line profile, the TCM experienced 0% tensile strain on X direction and 0% compression strain on X direction; for the dashed line profile, the TCM experienced 3% tensile strain on X direction and 1.5% compression strain on X direction.

For the LM and CAM, the opening and closing of the cracks that penetrated into the interface between the rigid thin film and PDMS substrate is useful in achieving the mechanical responsive optical properties. An alternative approach has been tried via casting liquid PDMS containing Rhodamine dye on the porous pure $TiO_2$ particulate film to prepare LM. Due to the low surface tension of liquid PDMS, the PDMS can effectively penetrate into the porous spacing of $TiO_2$ network. The resulting device does not show an eye-detectable fluorescence even stretched to 40% strain. The result follows from the absence of penetrated cracks in this system as stretched due to elastic nature of the PDMS infused $TiO_2$ thin film. Stretching this device can only slightly reduce the concentration of $TiO_2$ per unit area while the remaining substantial amount of $TiO_2$ still effectively blocks the UV light from travelling into PDMS/fluorophore layer. Thus, PVA was mixed with $TiO_2$ particles to form an impenetrable thin film for PDMS and the rigid nature of PVA/$TiO_2$ film allow the formation of cracks on thin film that penetrated into the interface as stretched. The UV blocking effect can be significantly reduced with applied strain to allow the UV travel through and excite the fluorescence in PDMS/fluorophore layer.

A series of mechanochromic devices with capabilities ranging from changing transparency, switchable luminescence, to altering coloration, revealing and concealing patterns in response to mechanical stimuli is provided. An aspect of the optical properties is to control strain-induced surface engineering, that is, the longitudinal crack opening and transverse invaginated folds. All of these devices are comprised of a rigid thin layer atop PDMS elastomer based on highly accessible, low-cost materials that can be facilely and quickly fabricated. For TCM, the folds and cracks with excellent light trapping and scattering capabilities can endow high opaqueness to the originally highly transparent samples. The evolution of crack opening and fold-ridge mechanisms are captured through FE analysis that incorporates damage and cracks in the rigid thin layer. For LM, the strain-tunable cracks on the UV shield layer act as "gates" to mediate the traveling of UV light to "switch on/off" the luminescence of mechanochromism. This device exhibits a remarkably high strain responsive sensitivity with a gauge factor of about 123.7, which is significantly higher than some of the strain sensors based on electrical resistance change, demonstrating an excellent sensing capability for detecting mechanical failure or damage. Two devices with capabilities of color alternation and encryption are also demonstrated here. All the mechanochromism are durable and reversible, which can preserve the strain responsive performance upon stretching and releasing for virtually infinite cycles within elasticity range. Strain-dependent cracks and folds on the rigid thin film of a series well-designed devices were used as examples to show how mechanically controlled surface engineering can achieve excellent mechanochromic optical performances.

Figure 18:
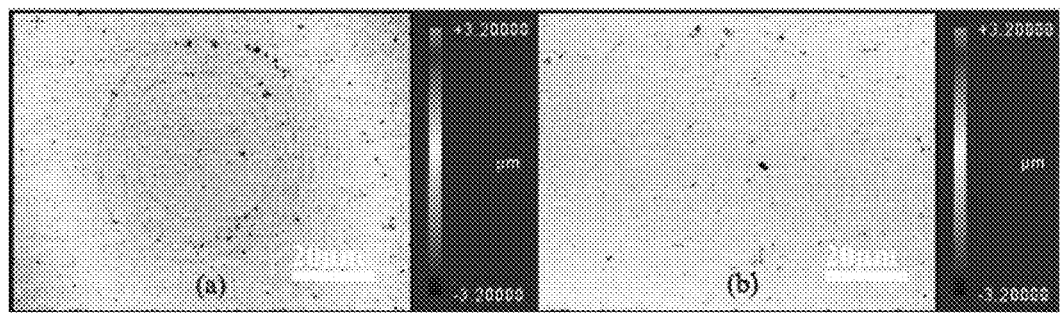
FIG. 18 shows (a) a dent imposed by a plastic tip; (b) the thin film surface recovering to be flat after being immersed in water for 30 minutes.

The presence of crosslinked PVA in between layers of laponite nanosheets allows the composite to have similar solvent induced shape memory properties as the neat crosslinked PVA. The pre-formed flat surface with crack and fold patterns are maintained by the laponite/PVA crosslinked network. Mechanical indentation (or abrasion) can leave micro-scale dents (or scratches). As shown in FIG. 18, a round dent was engendered by the indentation from a plastic tip. The round dent can be recovered to virtually original topography by spraying water droplets on the spot at room temperature for 45 minutes. Under external mechanical compression, internal stresses are generated among PVA chains. The stresses are frozen at room temperature due to the relatively high glass transition temperature (Tg, about 85° C.) of PVA. However, the frozen stresses can be released by water solvent stimuli, under a condition that water molecules can break the intermolecular hydrogen bonding of PVA chains and enhance the chain segment flexibility and mobility. Therefore, upon hydration, the once "frozen" molecular chain segments are allowed to slide, deform, or unfold back to the original stress-free state with the initial shape.

Preparation of TCM:

Transparent polyvinyl alcohol (PVA, MOWIOL 8-88, $M_w$~67,000 from Kuraray) and laponite (BYK Additives Inc., USA, Gonzales, Tex.) (mass ratio=1:4) composite films with a thickness of about 1.5 μm were cast on a pre-cleaned foundation followed by treatment with vinyltrimethoxysilane vapor for 2 h. Pure liquid polydimethylsiloxane (PDMS) (Sylgard-184, Dow Corning, base to curing agent ratio=10:1, thickness: ~1 mm) layer was then coated on PVA/laponite composite film and placed at room temperature for 12 h, followed by thermal curing at 80° C. for 2 h. The cured bilayer sheet was carefully peeled away from the foundation towards one direction. The peeling speed was controlled at about 10 mm/s at an angle of about 45°, and the peeling area was about 25 $cm^2$. It was then cut into rectangles (about 40 mm×10 mm) and mounted on a custom-built stretching tool. A pre-stretching of 60% uniaxial strain was applied along the initial peeling direction. The released sample was then ready for various performance tests.

Preparation of LM:

PVA (PVA, MOWIOL 8-88, $M_w$~67,000 from Kuraray) and $TiO_2$ (99.9%, CR828, Tronox) (mass ratio=1:4) composite films with a thickness of about 5.1 μm were spray-coated by an airbrush style spray-gun (Master Airbrush G444-SET, needle nozzle 0.5 mm and Royal Mini Air Compressors, TC-20B, 50 mg/mL PVA/$TiO_2$ aqueous suspension was used) on a pre-cleaned foundation followed by treatment with vinyltrimethoxysilane vapor for 2 h. A layer of PDMS/Rhodamine (99.9%, Alfa Aesar) composite film (Rhodamine concentration: $4.8×10^{-5}$ mol/g, thickness: ~1 mm) and a layer of PDMS/$TiO_2$ composite film (mass ratio=17:1, thickness ~1 mm) was then formed atop the $TiO_2$-PVA film by repeating the aforementioned drop casting and curing procedures. The PDMS layers all contain the same concentration of curing agent (base to curing agent ratio=10:1). The rest of the process was the same as TCM preparation.

Preparation of CAM:

A layer of PVA/laponite (mass ratio=1:4) composite film containing fluorescein (>90%, Alfa Aesar, fluorescein concentration: $1×10^{-8}$ mol/g) was drop cast on a pre-cleaned foundation prior to the spray coating of another layer of PVA/$TiO_2$ composite film (mass ratio=1:4) (total thickness of these two layers: ~13.9 μm) using the aforementioned airbrush style spray-gun followed by treatment with vinyltrimethoxysilane vapor for 2 h. The PDMS/$Y_2O_3$:$Eu^{3+}$ (>99%, Sigma Aldrich, dye concentration: $4.3×10^{-5}$ mol/g, thickness: ~1 mm) and PDMS/$TiO_2$ (mass ratio=17:1, thickness: ~1 mm) layers were drop cast atop the thin film by repeating the aforementioned drop casting and curing procedures. The PDMS layers all contain the same concentration of curing agent (base to curing agent ratio=10:1). The rest of the sample preparation is the same as the TCM.

Preparation of EM:

A layer of PVA/TiO$_2$ (mass ratio=1:4, thickness: ~5.1 μm) composite films were sprayed coated on a pre-cleaned foundation by aforementioned airbrush style spray-gun. A layer of PDMS/Rhodamine (Rhodamine concentration: 4.8× 10$^{-5}$ mol/g, thickness: ~1 mm) was then drop and cured atop the PVA/TiO$_2$ film. Subsequently, a thin layer of patterned TiO$_2$ film was spray coated with the assistance of a stencil mask atop the PDMS/Rhodamine layer. Finally, a layer of PDMS/carbon black (mass ratio=100:3, thickness ~1 mm) was deposited on the top of the aforementioned multilayer structure. The rest of the sample preparation is the same as the LM.

Fe Simulation:

The FE simulation of crack evolution using the commercial software ABAQUS (version 6.14). The schematic FE model for the folding in TCM is shown in FIG. 10. The geometric parameters and boundary conditions for the crack opening response are shown in the Table 1 and FIG. 12, respectively. A detailed discussion about the FE simulation for these two systems is described herein.

Characterization:

The mechanochromism samples were cut into rectangle shape (about 40 mm×10 mm) and mounted on a custom-built stretching tool to determine the optical performance. The morphology of the topmost rigid thin film with different strains under transmission mode (for LM and CAM) and reflective mode (for TCM) were recorded on an optical microscope (AmScope ME 520TA). The strain-dependent surface profile of the topmost rigid thin film of the TCM was examined on a ZYGO NewView 5000 non-contact white light profilometer. The strain-dependent transmittance test for the TCM was conducted on a Perkin Elmer ultraviolet/visible/near-infrared (UV/Vis/NIR) Lambda 900 spectrophotometer from 400 to 800 nm. Fluorescent spectra for LM and CAM were examined on a Jobin Yvon Fluorolog-3 fluorimeter with an excited light source at 365 nm or 247 nm. All of the digital photos and videos were captured by a Sony DSC-HX9V digital camera. All of the fluorescent samples were placed in a UVP Chromato-Vue C-70G UV viewing system with a UV light source of 365 nm or 254 nm for photographing or videotaping. Cyclic fatigue test of the samples were conducted on an Instron 5500 universal testing machine. Contact angle for TCM was tested on a Pendant Drop Tensiometer OCA 20 from Future Digital Scientific Corp.

Finite element simulation of the fold-ridge formation in TCM is described next. When the film-substrate system is subjected to the longitudinal tension, the bilayer material undergoes compression in the transverse direction due to the Poisson's effect, resulting in the formation of folds and ridges as evident in the experiment (see FIGS. 1 (d) and (e)). The computational model for the folding mechanism is similar to that for the crack evolution as shown in FIG. 10. The rigid thin film was tied onto the PDMS substrate by enforcing the displacement continuity across the interface. The unit cell contains the material of one crack spacing in the longitudinal tension direction and two folds in the transverse compression direction. The film-substrate system was subjected to a state of biaxial loading that a uniform tension was prescribed on the PDMS substrate in the X$_1$ direction, while a uniform compression was applied on both the film and substrate in the X$_3$ direction, as shown in FIG. 2 (a). Since both the film and the substrate are incompressible, the magnitude of the transverse compressive strain ($\varepsilon_3$) was assumed to be half of the longitudinal tensile strain ($\varepsilon_1$).

Although Applicant is not bound by any theory presented here, the reversible fold-ridge formation is believed to be a result of damage in the thin film. During the pre-stretch stage, the development of invaginated folds and sharp ridges caused damage spots at the edges and the valleys. As a result, the material at these locations was treated as a damaging solid by reducing the modulus to 1% of the modulus of the pristine thin film. The evolution of the deformed shape is shown in FIGS. 2 (a) and (c)-(f).

Finite element simulation of crack evolution in LM and CAM is described next. The crack opening response was simulated using the commercial software ABAQUS (version 6.14). The PDMS substrate was modeled as an incompressible hyperelastic material using the Arruda-Boyce model with a ground state shear modulus of 0.32 MPa and a locking parameter ($\lambda_m$) of 1.17. The rigid thin film, modeled as an incompressible elastic solid with a Young's modulus of 10 GPa, was tied onto the substrate by enforcing the displacement continuity at the interface. Both the PDMS substrate and the thin film were meshed using 3D hybrid linear elements, C3D8H. The distributed cracks on the thin film, which were developed after the pre-stretch procedure, were modeled as dummy nodes at the crack interface. These cracks were fully opened through the thin film and arrested in the PDMS substrate, as schematically shown in FIG. 12(a). In the present model, 10 parallel cracks were embedded along the loading direction, and the crack depth followed a normal distribution based on the average value and standard deviation measured from the experiment. The crack size during the deformation was determined by averaging the relative displacements of the two dummy nodes at the crack interface, d (see FIG. 12(a)), of the 10 cracks.

The boundary conditions for the film-substrate system subjected to uniaxial tension are shown in FIG. 12(b). A uniform displacement field is prescribed on the surface CDGF (U$_1$=δ), while the opposite surface (surface BAHE) is constrained along the x$_1$-direction (U$_1$=0). Additionally, point A is fixed (U$_1$=U$_2$=U$_3$=0) to prevent rigid body motion, and point B is restrained from moving along the x$_2$-direction (U$_2$=0). The film thickness, crack spacing, and crack depth used in the luminescent and color alteration mechanochromisms are summarized in Table 1. In each case, a film-to-substrate thickness ratio of 100:1 was maintained such that the PDMS substrate can be considered as an infinite medium.

The materials, methods, and uses are further illustrated by the following embodiments, which are non-limiting.

Embodiment 1

A mechanochromic system, comprising: a first inorganic/polymer composite layer; and a first elastomer layer bonded to the composite layer to form a composite/elastomer assembly.

Embodiment 1A

The system of Embodiment 1, wherein the polymer is water soluble.

Embodiment 1B

The system of Embodiment 1, wherein the polymer is organic soluble.

Embodiment 2

The system of Embodiment 1, wherein the polymer comprises polyvinylalcohol, polyvinyl butyral, polycarbonate, poly(methyl methacrylate), polyacrylates, polystyrene sulfonate, polyacrylic acid, polyethylenimine, any non-crosslinked polymer, or a combination comprising at least one of the foregoing.

Embodiment 3

The system of Embodiment 1, wherein the elastomer comprises polyurethane rubber, polyacrylate rubber, acrylic rubber, natural rubber, fluoroelastomers, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), polydimethylsiloxane (PDMS), or a combination comprising at least one of the foregoing.

Embodiment 3A

The system of Embodiment 3, wherein the fluoroelastomer comprises a copolymer of hexafluoropropylene and vinylidene fluoride; a terpolymer of tetrafluoroethylene, vinylidene fluoride and hexafluoropropylene; or comprises perfluoromethylvinylether.

Embodiment 4

The system of Embodiment 1, wherein the first inorganic/polymer composite layer comprises a 5:0.5 to 1:20 mass ratio of inorganic:polymer.

Embodiment 5

The system of Embodiment 1, wherein the polymer comprises polyvinylalcohol.

Embodiment 6

The system of Embodiment 1, wherein the elastomer comprises polydimethylsiloxane (PDMS).

Embodiment 7

The system of Embodiment 1, wherein the inorganic comprises titanium dioxide; laponite; aluminum oxide; magnesium oxide; zinc(II) oxide; montmorillonite; halloysite; kaolinite; Au; Pd; Ag; Al; or a combination comprising at least one of the foregoing.

Embodiment 8

The system of Embodiment 1, wherein the inorganic comprises laponite.

Embodiment 9

The system of Embodiment 1, wherein the mechanochromism is a transparency change, luminescence change, color change, encryption concealment change, or a combination comprising at least one of the foregoing.

Embodiment 10

The system of Embodiment 1, wherein the mechanochromism is a transparency change between transparent and opaque.

Embodiment 11

The system of Embodiment 1, wherein the mechanochromism is a luminescence change, wherein the first elastomer layer comprises a fluorophore, forming a elastomer/fluorophore layer, and the assembly further comprises an ultraviolet shielding layer connected to a top surface of the elastomer/fluorophore layer, and the assembly further comprises a second elastomer layer bonded to the bottom surface of the elastomer/fluorophore layer, wherein the second elastomer layer comprises a shielding and reflective layer.

Embodiment 11A

The system of Embodiment 1, wherein the fluorophore comprises a rhodamine; a fluorescein; a coumarin; a cyanine; a quinine; a anthraquinine; an acridine; an oxazine; a fluorone; a phenanthridine; or a combination comprising at least one of the foregoing.

Embodiment 12

The system of Embodiment 11, wherein the elastomer is polydimethylsiloxane (PDMS).

Embodiment 13

The system of Embodiment 11, wherein the ultraviolet shielding layer comprises PVA/titanium dioxide and the shielding and reflective layer on the second elastomer layer comprises polydimethylsiloxane/titanium dioxide.

Embodiment 14

The system of Embodiment 1, wherein the mechanochromism is color change, wherein the assembly further comprises: a second inorganic/polymer composite layer connected to the top surface of the first inorganic/polymer composite layer; a second elastomer layer bonded to the bottom surface of the first elastomer layer, wherein the second elastomer layer comprises a shielding and reflective layer; and wherein the second inorganic/polymer composite layer comprises a fluorophore, and wherein the first elastomer layer comprises a fluorescent material.

Embodiment 15

The system of Embodiment 14, wherein the fluorescent material comprises cerium magnesium aluminate doped with terbium ($CeMgAl_{11}O_{19}$:Tb (CAT)); lanthanum phosphate doped with cerium and terbium ($LaPO_4$:Ce, Tb (LAP)); cerium gadolinium magnesium pentaborate doped with terbium ((Ce, Gd, Tb)$MgB_5O_{10}$(CBT)); yttrium oxide doped with europium ($Y_2O_3$:Eu (YOE or L581)); germanium zinc magnesium pentaborate ($GeZnMgB_5O_{10}$:Ce, Mn (L165)), any fluorescent material, or a combination comprising at least one of the foregoing.

Embodiment 16

The system of Embodiment 1, wherein the fluorescent material comprises $Y_2O_3:Eu^{3+}$.

Embodiment 17

The system of Embodiment 14, wherein the fluorophore is fluorescein.

Embodiment 18

The system of Embodiment 1, wherein the mechanochromism is encryption concealment change, and the first elastomer layer comprises a fluorophore, forming a elastomer/fluorophore layer, wherein the first inorganic/polymer composite layer is connected to a top surface of the elastomer/fluorophore layer; and wherein the assembly further comprises a patterned shielding and reflective layer connected to the bottom surface of the elastomer/fluorophore layer; and a reflective layer connected to a bottom surface of the patterned shielding and reflective layer.

Embodiment 19

The system of Embodiment 18, wherein the first inorganic/polymer composite layer comprises PVA/titanium dioxide; the fluorophore comprises rhodamine; the patterned shielding and reflective layer comprises titanium dioxide; and the reflective layer comprises polydimethylsiloxane/carbon black.

Embodiment 20

The system of Embodiment 1, wherein the first elastomer layer is 0.1 to 3.5 millimeters thick.

Embodiment 21

The system of Embodiment 1, wherein the composite layer is 1 to 30 micrometers thick.

Embodiment 22

A method of making a mechanochromic system, comprising: applying a layer of inorganic/polymer composite on a substrate; applying a layer of elastomer on a top surface of the composite to form a composite/elastomer assembly; curing the composite/elastomer assembly; and removing the composite/elastomer assembly from the substrate.

Embodiment 23

The system of Embodiment 22, wherein the curing is for 10 to 14 hours at room temperature, and for 1 to 3 hours at 70 to 90° C.

Embodiment 24

The system of Embodiment 22, wherein the polymer comprises polyvinylalcohol and the elastomer comprises polydimethylsiloxane (PDMS).

Embodiment 25

The system of Embodiment 22, wherein the curing is for 11 to 13 hours at room temperature, and for 1.5 to 2.5 hours at 75 to 85° C.

Embodiment 26

The system of Embodiment 22, wherein the inorganic/polymer composite comprises 70 to 90 wt % laponite, where the wt % is based on the total weight of the composite.

Embodiment 27

The system of Embodiment 22, further comprising applying a 50 to 70% uniaxial tensile pre-stretch to the composite/elastomer; and releasing the pre-stretch.

Embodiment 28

A method of using a mechanochromic system, comprising: providing a composite/elastomer assembly of any of Embodiments 1 to 21; applying a 50 to 70% uniaxial tensile pre-stretch to the composite/elastomer film; releasing the pre-stretch; applying an up to 50% uniaxial tensile strain to the composite/elastomer film, wherein the mechanochromic system undergoes a reversible transparency change, fluorescent luminescence change, fluorescent color change, encryption concealment change, or a combination comprising at least one of the foregoing.

Embodiment 29

The use of a mechanochromic system of any one or more of Embodiments 1 to 21 in a smart window, self-cleaning surface, strain sensor, encryption device, display optics, or a toy.

The singular forms "a," "an," and "the" include plural referents unless the context clearly dictates otherwise. "Or" means "and/or." The modifier "about" used in connection with a quantity is inclusive of the stated value and has the meaning dictated by the context (e.g., includes the degree of error associated with measurement of the particular quantity). Unless otherwise specified, the terms "first," "second," and the like, as used herein do not denote any order, quantity, or importance, but rather are used to distinguish one element from another.

The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. The suffix "(s)" is intended to include both the singular and the plural of the term that it modifies, thereby including at least one of that term (e.g., the colorant(s) includes at least one colorants). "Optional" or "optionally" means that the subsequently described event or circumstance can or can not occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All publications, patents, and patent applications cited in this specification are herein incorporated by reference, and for any and all purposes, as if each individual publication, patent or patent application were specifically and individually indicated to be incorporated by reference. In the case of inconsistencies, the present disclosure will prevail.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A mechanochromic system, comprising:
a first inorganic and polymer composite layer, wherein the polymer comprises polyvinylalcohol, polyvinyl butyral, polycarbonate, poly(methyl methacrylate), polyacrylates, polystyrene sulfonate, polyacrylic acid, polyethylenimine, any non-crosslinked polymer, or a combination comprising at least one of the foregoing; and the first inorganic and polymer composite layer comprises a 5:0.5 to 1:20 mass ratio of inorganic:polymer; and
a first elastomer layer comprising an elastomer, the first elastomer layer bonded to the first inorganic and polymer composite layer to form a composite and elastomer assembly,
wherein the elastomer comprises polyurethane rubber, polyacrylate rubber, acrylic rubber, natural rubber, fluoroelastomer, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), polydimethylsiloxane (PDMS), or a combination comprising at least one of the foregoing;
wherein the first elastomer layer is 0.1 to 3.5 millimeters thick and the first inorganic and polymer composite layer is 1 to 30 micrometers thick; and
wherein the first inorganic and polymer composite layer is rigid relative to the first elastomer layer.

2. The system of claim 1, wherein the polymer is water soluble or organic soluble.

3. The system of claim 1, wherein the fluoroelastomer comprises a copolymer of hexafluoropropylene and vinylidene fluoride; a terpolymer of tetrafluoroethylene, vinylidene fluoride and hexafluoropropylene; perfluoromethylvinylether; or
a combination comprising at least one of the foregoing.

4. The system of claim 1, wherein the polymer comprises polyvinylalcohol.

5. The system of claim 1, wherein the elastomer comprises polydimethylsiloxane (PDMS).

6. The system of claim 1, wherein the inorganic comprises titanium dioxide; laponite; aluminum oxide; magnesium oxide; zinc(II) oxide; montmorillonite; halloysite; kaolinite; Au; Pd; Ag; Al; or a combination comprising at least one of the foregoing.

7. The system of claim 1, wherein the mechanochromic system exhibits mechanochromism, wherein the mechanochromism is a transparency change, luminescence change, color change, encryption concealment change, or a combination comprising at least one of the foregoing.

8. The system of claim 7, wherein the mechanochromism is a transparency change between transparent and opaque.

9. A mechanochromic system, comprising:
a first inorganic and polymer composite layer, wherein the polymer comprises polyvinylalcohol, polyvinyl butyral, polycarbonate, poly(methyl methacrylate), polyacrylates, polystyrene sulfonate, polyacrylic acid, polyethylenimine, any non-crosslinked polymer, or a combination comprising at least one of the foregoing; and the first inorganic and polymer composite layer comprises a 5:0.5 to 1:20 mass ratio of inorganic:polymer; and
a first elastomer layer comprising an elastomer, the first elastomer layer bonded to the first inorganic and polymer composite layer to form a composite and elastomer assembly,
wherein the elastomer comprises polyurethane rubber, polyacrylate rubber, acrylic rubber, natural rubber, fluoroelastomer, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MB S), high rubber graft (HRG), polydimethylsiloxane (PDMS), or a combination comprising at least one of the foregoing;
wherein the first inorganic and polymer composite layer is rigid relative to the first elastomer layer, and
wherein the mechanochromic system exhibits a mechanochromism that is a luminescence change, wherein the first elastomer layer further comprises a fluorophore and the first inorganic and polymer composite layer exhibits an ultraviolet shielding property, and the composite and elastomer assembly further comprises a second elastomer layer bonded to a surface of the first elastomer layer opposite to the first inorganic and polymer composite layer, wherein the second elastomer layer exhibits a shielding property, a reflective property, or both shielding and reflective properties.

10. The system of claim 9, wherein the fluorophore comprises a rhodamine; a fluorescein; a coumarin; a cyanine; a quinine; a anthraquinine; an acridine; an oxazine; a fluorone; a phenanthridine; or a combination comprising at least one of the foregoing.

11. The system of claim 9, wherein the first inorganic and polymer composite layer comprises PVA and titanium dioxide, and the second elastomer layer comprises polydimethylsiloxane and titanium dioxide.

12. The system of claim 9, wherein the first elastomer layer is 0.1 to 3.5 millimeters thick and wherein the first inorganic and polymer composite layer is 1 to 30 micrometers thick.

13. A mechanochromic system, comprising:
a first inorganic and polymer composite layer, wherein the polymer comprises polyvinylalcohol, polyvinyl butyral, polycarbonate, poly(methyl methacrylate), polyacrylates, polystyrene sulfonate, polyacrylic acid, polyethylenimine, any non-crosslinked polymer, or a combination comprising at least one of the foregoing; and the first inorganic and polymer composite layer comprises a 5:0.5 to 1:20 mass ratio of inorganic:polymer; and a first elastomer layer comprising an elastomer, the first elastomer layer bonded to the first inorganic and polymer composite layer to form a composite and elastomer assembly, wherein the elastomer comprises polyurethane rubber, polyacrylate rubber, acrylic rubber, natural rubber, fluoroelastomer, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), polydimethylsiloxane (PDMS), or a combination comprising at least one of the foregoing;

wherein the first inorganic and polymer composite layer is rigid relative to the first elastomer layer, and wherein the mechanochromic system exhibits a mechanochromism that is a color change, wherein the composite and elastomer assembly further comprises:

a second inorganic and polymer composite layer connected to a top surface of the first inorganic and polymer composite layer opposite to the first elastomer layer;

a second elastomer layer bonded to a bottom surface of the first elastomer layer opposite to the first inorganic and polymer composite layer, wherein the second elastomer layer exhibits a shielding property, a reflective property, or both shielding and reflective properties; and wherein the second inorganic and polymer composite layer comprises a fluorophore, and wherein the first elastomer layer further comprises a fluorescent material.

14. The system of claim 13, wherein the first elastomer layer is 0.1 to 3.5 millimeters thick and wherein the first inorganic and polymer composite layer is 1 to 30 micrometers thick.

15. The system of claim 13, wherein the fluorescent material of the first elastomer layer comprises cerium magnesium aluminate doped with terbium; lanthanum phosphate doped with cerium and terbium; cerium gadolinium magnesium pentaborate doped with terbium; yttrium oxide doped with europium; germanium zinc magnesium pentaborate, or a combination comprising at least one of the foregoing.

16. The system of claim 15, wherein the fluorescent material of the first elastomer layer comprises $Y_2O_3:Eu^{3+}$ and wherein the fluorophore of the second inorganic and polymer composite layer is fluorescein.

17. A mechanochromic system, comprising:

a first inorganic and polymer composite layer, wherein the polymer comprises polyvinylalcohol, polyvinyl butyral, polycarbonate, poly(methyl methacrylate), polyacrylates, polystyrene sulfonate, polyacrylic acid, polyethylenimine, any non-crosslinked polymer, or a combination comprising at least one of the foregoing; and the first inorganic and polymer composite layer comprises a 5:0.5 to 1:20 mass ratio of inorganic:polymer; and a first elastomer layer comprising an elastomer, the first elastomer layer bonded to the first inorganic and polymer composite layer to form a composite and elastomer assembly, wherein the elastomer comprises polyurethane rubber, polyacrylate rubber, acrylic rubber, natural rubber, fluoroelastomer, ethylene-propylene rubber (EPR), ethylene-butene rubber, ethylene-propylene-diene monomer rubber (EPDM), epichlorohydrin rubber, acrylate rubbers, hydrogenated nitrile rubber (HNBR), silicone elastomers, polyether block amides, ethylene vinyl acetate, styrene-butadiene-styrene (SBS), styrene-butadiene rubber (SBR), styrene-(ethylene-butene)-styrene (SEBS), acrylonitrile-butadiene-styrene (ABS), acrylonitrile-ethylene-propylene-diene-styrene (AES), styrene-isoprene-styrene (SIS), styrene-(ethylene-propylene)-styrene (SEPS), methyl methacrylate-butadiene-styrene (MBS), high rubber graft (HRG), polydimethylsiloxane (PDMS), or a combination comprising at least one of the foregoing;

wherein the first inorganic and polymer composite layer is rigid relative to the first elastomer layer, and wherein the mechanochromic system exhibits a mechanochromism that is an encryption concealment change, and the first elastomer layer further comprises a fluorophore, wherein the first inorganic and polymer composite layer is connected to a top surface of the first elastomer layer; and wherein the composite and elastomer assembly further comprises a patterned layer connected to a bottom surface of the first elastomer layer, wherein the patterned layer exhibits a shielding property, a reflective property, or both shielding and reflective properties; and a reflective layer connected to a bottom surface of the patterned layer.

18. The system of claim 17, wherein the first inorganic and polymer composite layer comprises PVA and titanium dioxide; the fluorophore comprises rhodamine; the patterned layer comprises titanium dioxide; and the reflective layer comprises polydimethylsiloxane and carbon black.

19. The system of claim 17, wherein the first elastomer layer is 0.1 to 3.5 millimeters thick and wherein the first inorganic and polymer composite layer is 1 to 30 micrometers thick.

* * * * *